United States Patent
Meier et al.

(10) Patent No.: US 9,156,768 B2
(45) Date of Patent: Oct. 13, 2015

(54) ISOLATION OF ACRYLIC ACID BY MEANS OF A DISTILLATION COLUMN HAVING A SIDE OFFTAKE

(75) Inventors: Ralf Meier, Dortmund (DE); Juergen Mosler, Marl (DE)

(73) Assignee: Evonik Degussa GmbH, Essen (DE)

( * ) Notice: Subject to any disclaimer, the term of this patent is extended or adjusted under 35 U.S.C. 154(b) by 169 days.

(21) Appl. No.: 13/697,127

(22) PCT Filed: Apr. 7, 2011

(86) PCT No.: PCT/EP2011/055429
§ 371 (c)(1),
(2), (4) Date: Jan. 29, 2013

(87) PCT Pub. No.: WO2011/141240
PCT Pub. Date: Nov. 17, 2011

(65) Prior Publication Data
US 2013/0118892 A1    May 16, 2013

(30) Foreign Application Priority Data

May 10, 2010 (DE) .......................... 10 2010 028 781

(51) Int. Cl.
*C07C 51/46* (2006.01)
*C07C 57/04* (2006.01)
(Continued)

(52) U.S. Cl.
CPC ............... *C07C 51/46* (2013.01); *B01D 3/141* (2013.01); *B01D 3/143* (2013.01); *B01D 3/36* (2013.01); *C07C 51/44* (2013.01); *C07C 57/04* (2013.01); *Y10S 203/19* (2013.01); *Y10S 203/21* (2013.01)

(58) Field of Classification Search
CPC .......... B01D 3/141; B01D 3/143; B01D 3/36; C07C 51/44; C07C 51/46; C07C 51/50; C07C 57/04; Y10S 203/19; Y10S 203/21
See application file for complete search history.

(56) References Cited

U.S. PATENT DOCUMENTS 2,050,235 A * 8/1936 Othmer .......................... 562/608
2,859,154 A * 11/1958 Othmer .......................... 203/35
(Continued)

FOREIGN PATENT DOCUMENTS

DE    199 24 533    11/2000
DE    101 38 150    2/2003
(Continued)

OTHER PUBLICATIONS

International Search Report Issued Sep. 28, 2011 in PCT/EP11/055429 Filed Apr. 7, 2011.
(Continued)

*Primary Examiner* — Virginia Manoharan
(74) *Attorney, Agent, or Firm* — Oblon, McClelland, Maier & Neustadt, L.L.P.

(57) ABSTRACT

The present process separates acrylic acid from a composition containing acrylic acid and at least one accompanying product. The process first involves contacting the composition with an aqueous liquid stream to give a liquid solution of acrylic acid, accompanying product, and water. The water then forms an azeotrope with an entrainer, which is added to the solution. Distillation then separates the solution into an overhead product containing the azeotrope and a bottom product containing acrylic acid and accompanying product. The overhead product is separated into water and entrainer and the bottom product is separated in a distillation column into acrylic acid and accompanying product. The process provides a way to remove high- and low-boiling products with a small number of distillation columns.

8 Claims, 3 Drawing Sheets

(51) Int. Cl.
*B01D 3/36* (2006.01)
*B01D 3/14* (2006.01)
*C07C 51/44* (2006.01)

(56) References Cited

U.S. PATENT DOCUMENTS

| | | | | |
|---|---|---|---|---|
| 3,414,485 | A | * | 12/1968 | Speed .............................. 203/43 |
| 3,433,831 | A | * | 3/1969 | Aoshima et al. .............. 562/600 |
| 7,265,241 | B2 | | 9/2007 | Yada et al. |
| 7,294,741 | B2 | | 11/2007 | Bub et al. |
| 7,557,245 | B2 | | 7/2009 | Nordhoff et al. |
| 7,557,246 | B2 | | 7/2009 | Nordhoff et al. |
| 8,178,717 | B2 | | 5/2012 | Balduf et al. |
| 8,309,668 | B2 | | 11/2012 | Balduf et al. |
| 2003/0146081 | A1 | * | 8/2003 | Aldrett et al. .................... 203/57 |
| 2004/0225152 | A1 | | 11/2004 | Yada et al. |
| 2004/0236049 | A1 | | 11/2004 | Fuchs et al. |
| 2007/0262022 | A1 | | 11/2007 | Mosler et al. |
| 2007/0295591 | A1 | | 12/2007 | Mosler |
| 2009/0253934 | A1 | | 10/2009 | Ho et al. |
| 2010/0273970 | A1 | | 10/2010 | Koestner et al. |
| 2011/0046297 | A1 | | 2/2011 | Hengstermann et al. |
| 2011/0124855 | A1 | | 5/2011 | Hengstermann et al. |

FOREIGN PATENT DOCUMENTS

| | | |
|---|---|---|
| EP | 2 085 376 | 8/2009 |
| TW | 200948774 A1 | 12/2009 |
| WO | 03 051809 | 6/2003 |
| WO | 03 078378 | 9/2003 |
| WO | 2005 092463 | 10/2005 |
| WO | 2005 092464 | 10/2005 |
| WO | 2006 008083 | 1/2006 |
| WO | 2007 020024 | 2/2007 |
| WO | 2009 095111 | 8/2009 |
| WO | 2009 130085 | 10/2009 |
| WO | 2010 063529 | 6/2010 |
| WO | 2010 107284 | 9/2010 |
| WO | 2011 141240 | 11/2011 |
| WO | 2012 076505 | 6/2012 |

OTHER PUBLICATIONS

U.S. Appl. No. 14/105,237, filed Dec. 13, 2013, Cameretti, et al.
U.S. Appl. No. 14/105,587, filed Dec. 13, 2013, Cameretti, et al.
Office Action issued on Oct. 31, 2014 in the corresponding Chinese Patent Application No. 201180023313.3 (with English Translation).
Combined Taiwanese Examination Report and Search Report issued Feb. 9, 2015 in Patent Application No. 100116124 (submitting English language translation only).

* cited by examiner

ISOLATION OF ACRYLIC ACID BY MEANS OF A DISTILLATION COLUMN HAVING A SIDE OFFTAKE

The invention relates to a process for separating acrylic acid from a composition comprising acrylic acid and at least one accompanying product, which has the features a) to e) of claim 1. A process of this type is known both from U.S. Pat. No. 5,910,607 and from U.S. Pat. No. 7,189,872.

Acrylic acid (prop-2-enoic acid) is a basic building block for the production of superabsorbents which are used primarily in hygiene products. It is obtained on an industrial scale by catalytic vapour-phase reaction of propene with oxygen. This forms the desired acrylic acid together with undesirable accompanying products which are a hindrance in the further processing of the acrylic acid. These accompanying products are essentially acetic acid, aldehydes and water. An important step in the preparation of acrylic acid is accordingly freeing the acrylic acid-containing composition from the vapour-phase reaction of the undesirable accompanying products so as to leave pure acrylic acid. The invention is concerned with this purification.

Since acrylic acid has a strong tendency to polymerize, a stabilizing inhibitor always has to be added thereto. In the generic process described in U.S. Pat. No. 7,189,872, the work-up by distillation of the bottom product which has been dewatered by means of an entrainer is carried out by means of three distillation columns which are connected in series and which successively separate off the low- and high-boiling accompanying products from the stream. Owing to the large number of distillation columns, such a plant is comparatively expensive to install and to operate; the energy and inhibitor consumption increases with the number of columns.

U.S. Pat. No. 5,910,607 addresses merely the removal of the low-boiling acetic acid from the dewatered bottom product by distillation. No details are provided regarding the removal of high-boiling accompanying products such as aldehydes.

EP2085376A1 discloses a process for purifying methacrylic acid. A significant difference from the purification of acrylic acid is that the polymerization potential of monomeric acrylic acid is significantly higher than that of methacrylic acid and lower thermal stresses and thus lower process temperatures accordingly have to be adhered to for the work-up of acrylic acid. For this reason, the purification of methacrylic acid is not really technically comparable to that of acrylic acid.

In the light of this prior art, it is an object of the present invention to develop a process of the type mentioned at the outset in such a way that a very small number of distillation columns is adequate for the purification of the previously dewatered bottom product and a reliable removal of the high- and low-boiling accompanying products is nevertheless obtained.

This object is achieved by the fractional distillation of the bottom product being carried out in a distillation column which is provided with a side offtake and from the bottom of which the high-boiling constituents of the accompanying product are taken off and from the top of which the low-boiling constituents of the accompanying product are taken off and from the side offtake of which the acrylic acid is taken off.

The invention accordingly provides a process for separating acrylic acid from a composition containing acrylic acid and at least one accompanying product, a) in which the composition is firstly contacted with an aqueous liquid stream in such a way that a liquid solution containing acrylic acid, accompanying product and water is obtained, b) in which an entrainer which forms a heterogeneous minimum azeotrope with the water of the liquid solution is added to the liquid solution, c) in which the liquid solution is separated by distillation into an overhead product containing the minimum azeotrope and a bottom product containing acrylic acid and accompanying product, d) in which the overhead product is separated into water and recirculatable entrainer e) and in which the bottom product is separated by distillation into acrylic acid and accompanying product, f) wherein the fractional distillation of the bottom product is carried out in a distillation column which has a side offtake and from the bottom of which high-boiling constituents of the accompanying product are taken off, from the top of which low-boiling constituents of the accompanying product are taken off and from the side offtake of which the acrylic acid is taken off.

The present invention is based, inter alia, on the recognition that both low-boiling accompanying products and high-boiling accompanying products can be removed from the dewatered bottom product in a single distillation column when this distillation column is provided with a side offtake from which the purified acrylic acid is taken off.

Compared to U.S. Pat. No. 7,189,872, the outlay in terms of apparatus necessary for purifying the acrylic acid can be minimized while maintaining the purity achieved in this prior art thanks to the use of the distillation column having a side offtake. This reduces not only the capital costs but also the operating costs.

According to the invention, the acrylic acid can be taken off from the side offtake either in liquid form or in gaseous form.

Taking the acrylic acid off in gaseous form is preferred since this further reduces the proportion of high boilers in the target product. Taking off liquid acrylic acid having a low proportion of high boilers from the side of the distillation column is possible when the distillation column is configured as a dividing wall column. A dividing wall column is a distillation column which has a dividing wall extending essentially vertically through the column. Such a dividing wall column is described in U.S. Pat. No. 2,471,134.

Different structural variants of a dividing wall column are suitable; these differ in terms of the arrangement of the dividing wall:

Firstly, it is possible for the dividing wall not to extend over the full height of the distillation column but instead only from a dividing wall-free top region to a dividing wall-free bottom region. Accordingly, free transfer of the feed over the entire cross section of the column is possible in a region close to the top and in a region close to the bottom. The dividing wall-free top region preferably extends over the upper 10% of the plates in the column, and the dividing wall-free bottom region preferably extends over the lower 10-20% of the plates of the column. The purpose of this configuration is that low- and high-boilers can be separated off by use of only one condenser and one vaporizer.

A column which is free of a dividing wall in the top region and bottom region can advantageously be modified so that the part of the distillation column located on the side of the side offtake is closed off from the dividing wall-free top region by a barrier wall. This has the advantage that impurities which are present on the feed side above the feed position in the column cannot go over into the upper region on the side stream side and reduce the product purity in the side stream.

In a further embodiment, a dividing wall-free bottom region is omitted so that the dividing wall extends from the dividing wall-free top region down to the floor of the bottom. This variant has the advantage that components which are present on the feed side below the feed point cannot go over into the lower region on the side stream side. A higher product purity is achieved in this way.

In dimensioning the dividing walls of all embodiments of the dividing wall column, it is necessary to observe the design rule that the dividing wall has to extend from a height level above the side offtake to a height level below the level of the bottom product introduced into the distillation column. As a consequence, the inlet for the bottom product to be separated in the dividing wall column is shielded by the dividing wall from the side offtake, i.e. the outlet for the acrylic acid, so that a direct flow of material from the inlet for the bottom product to the outlet is prevented. This measure is the prerequisite for a good separation performance.

The process of the invention is particularly suitable for purifying a composition which comprises acetic acid and/or water and/or aldehydes as accompanying products in addition to acrylic acid. Acetic acid is a low-boiling accompanying product which is taken off from the top of the distillation column, while the aldehydes are high boilers which are taken off from the bottom of the distillation column provided with a side offtake.

A suitable entrainer is an organic solvent having a boiling point in the range from 80 to 130° C., for example toluene or heptane or cyclohexane or methyl-cyclohexane.

The fractional distillation of the liquid solution in a dewatering column is preferably carried out by setting the heating power and amount of entrainer in such a way that the bottom product is virtually water-free and the concentration of the entrainer in the bottom product is from 1 to 15% by weight, preferably from 8 to 12% by weight. In this context, "virtually water-free" means less than 0.5% by weight, better from 0.05 to 0.3% by weight. This concentration range is characterized by particularly advantageous operation. Firstly, low degrees of polymerization are observed because of the relatively low temperatures at the bottom. Secondly, it is found that, under these process parameters, undesirable polymer is preferably obtained in the readily accessible bottom region of the column. Owing to the very good accessibility, the column can be freed of the polymer and other deposits with little expenditure of time and money in the event of a shutdown for cleaning and optimum plant availability is achieved. The invention will now be illustrated by means of examples. Here:

FIG. 1 schematically shows a plant for carrying out the process;

Figure 1:
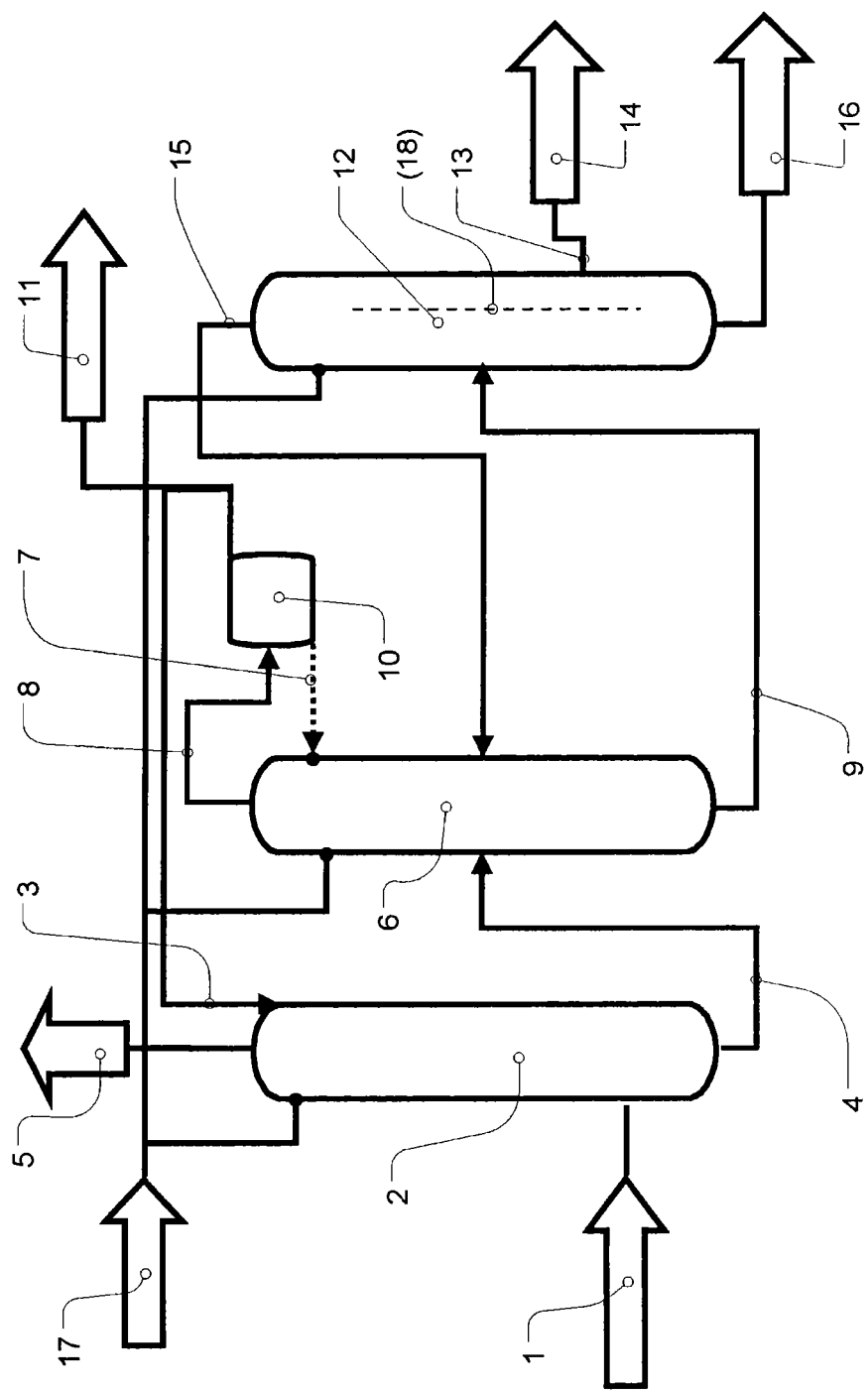

A plant for carrying out the process of the invention is shown schematically in FIG. 1. The starting material is a gaseous composition 1 coming from a reactor which is not shown and containing acrylic acid and accompanying product comprising, in particular, acetic acid, water and aldehydes. In a quenching column 2, the composition 1 is contacted with an aqueous liquid stream 3 to form a liquid solution 4 composed of water (from 20 to 80% by weight), acrylic acid (40-80% by weight) and various condensable accompanying products such as acetic acid (from 1 to 5% by weight) and aldehydes. Uncondensable constituents of the composition 1 leave the quenching column 2 at the top as gas stream 5.

In the next process step, the aqueous liquid stream 3 is fed to a dewatering column 6. With addition of an entrainer 7 which forms a heterogeneous minimum azeotrope with the water, the water/entrainer azeotrope is separated off as vapour at the top of the dewatering column 6. The dewatering column 6 preferably has from 5 to 20 theoretical plates. The pressure at the top of the dewatering column 6 is in the range from 133 to 400 hPa, and the temperature at the bottom is below 100° C. The process variables heating power and amount of entrainer are set so that a virtually water-free bottom product 9 (water content less than 0.5% by weight, preferably from 0.05 to 0.3% by weight) having an entrainer concentration of from 1 to 15% by weight, preferably from 8 to 12% by weight, is obtained. The advantages of this concentration range have been highlighted above.

The gaseous water/entrainer azeotrope 8 is condensed to form two liquid phases (not shown) and goes into a decanter 10 in which the two phases entrainer 7 and water are separated. The entrainer 7 is recirculated to the dewatering column 6, and the water partly goes as aqueous liquid stream 3 back to the quenching column 2 and an excess is discharged as wastewater 11.

The bottom product 9 from the dewatering column 6, which comprises mainly acrylic acid, acetic acid and high-boiling aldehydes, is fed, for the purposes of further purification, to a distillation column 12 in which further low boilers are separated off at the top and high boilers are separated off at the bottom. For this purpose, the distillation column 12 is provided with a side offtake 13 from which the purified acrylic acid 14 is taken off in vapour or liquid form.

Operating parameters and constructions of the distillation column 12 will be discussed below. The low-boiling constituents 15 of the accompanying product such as acetic acid which have been taken off at the top of the distillation column 15 are recirculated to the dewatering column 6. The high-boiling constituents 16 of the accompanying product are discharged from the bottom of the distillation column 12.

In contrast to the prior art described, the number of process steps for the isolation of pure acrylic acid 14 is minimized in the process of the invention. Apart from the low capital costs, low energy consumptions and also a lower requirement for polymerization inhibitors 17 which have to be introduced in every distillation step are obtained because of the smaller number of process steps. In addition, the monomeric acrylic acid is subjected to less thermal stress. This reduces the polymerization of the acrylic acid and the formation of acrylic acid dimers, which in turn increases the product yield.

In addition, the division of the low boiler removal into the removal in the dewatering column 6 with a remaining residual concentration of entrainer and the combined low/high boiler removal in the distillation column 12 having a side offtake leads to the polymeric residues which are unavoidably formed being obtained in the very readily accessible bottom of the dewatering column 6. Removal of the polymer and cleaning of the column can be carried out with relatively little difficulty in this region, and downtimes of the plant are therefore minimized.

Configuration and operating parameters of the distillation column 12 having a side offtake 13 will now be explained:

The distillation column 12 should have from 30 to 45 practical plates. The side offtake 13 should be at a height level which corresponds to from 70 to 80% of the total number of plates (counted from the top). The pressure at the top should be from 40 to 50 hPa, and the temperature at the top should be the range from 35 to 50° C. Vaporization at the bottom of the distillation column 12 is effected by means of a circulation vaporizer (product temperature less than 90° C.) and a subsequent thin film evaporator (product temperature less then 125° C., preferably 115° C.).

Figure 2:
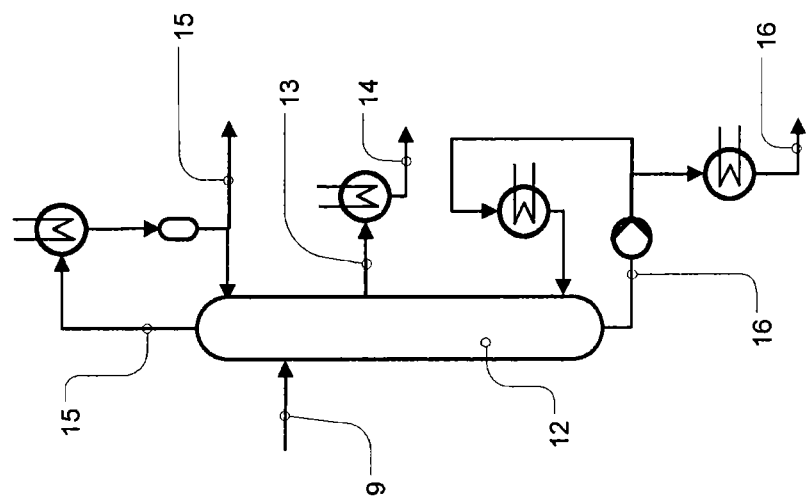
FIG. 2 shows an embodiment of a distillation column with side offtake and without dividing wall.

If the acrylic acid 14 is taken off in gaseous form, a dividing wall-free column as shown in FIG. 2 can be used. The bottom stream 9 is then fed into the distillation column 12 at a height level above the side offtake 13.

Figure 5:
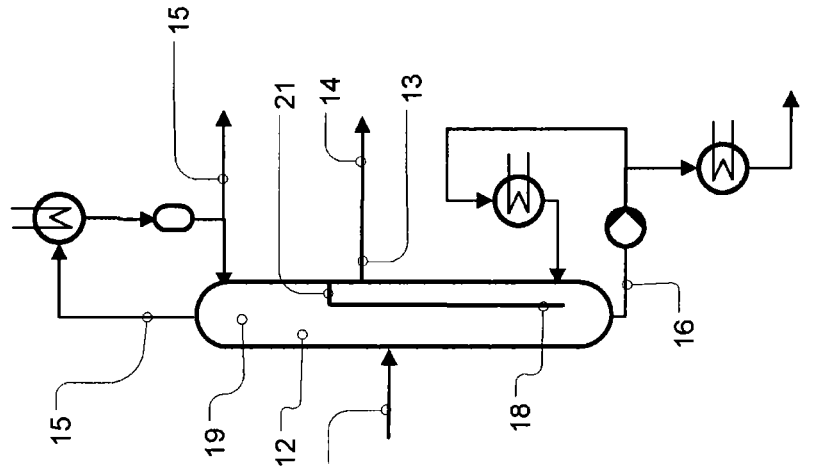
FIG. 5 shows an embodiment of a distillation column with side offtake and a dividing wall between dividing wall-free top region and bottom region, additionally with a barrier plate on the side offtake side.
Figure 4:
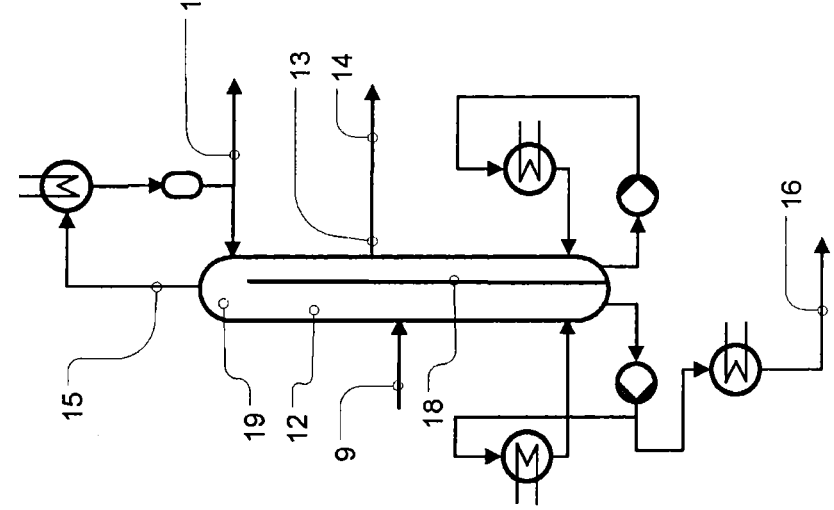
FIG. 4 shows an embodiment of a distillation column with side offtake and a dividing wall from the dividing wall-free top region to the floor of the bottom.
Figure 3:
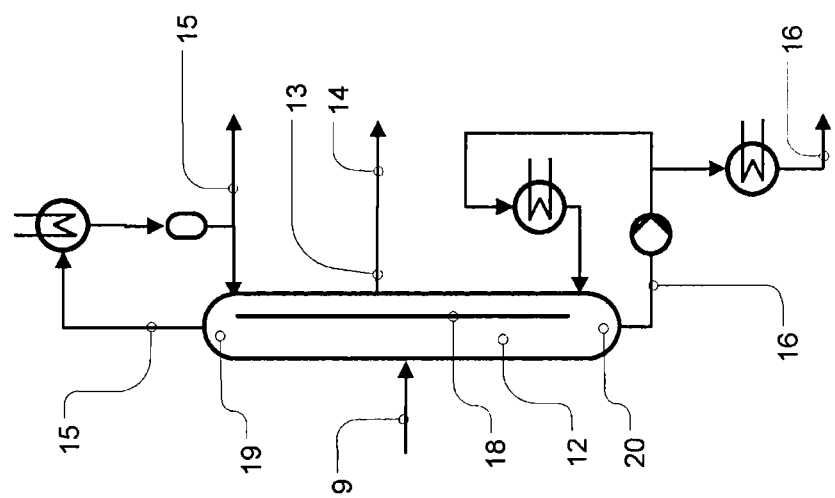
FIG. 3 shows an embodiment of a distillation column with side offtake and a dividing wall between dividing wall-free top region and bottom region.

Taking off the acrylic acid 14 in the liquid state requires a distillation column 12 equipped with a dividing wall 18; cf. FIGS. 3, 4 and 5. In a dividing wall column, the bottom stream 9 is fed into the distillation column 12 at a height level below the height level of the side offtake 13. The dividing wall 18 always has to be dimensioned so that it extends from a height level above the level of the side offtake to a height level below the level of the bottom product 9 introduced into the distillation column 12. The upper 10% of the plates form a dividing wall-free top region 19 below which the dividing wall 18 begins.

The dividing wall 18 ends, in the example shown in FIG. 3, at a dividing wall-free bottom region 20 which corresponds approximately to the bottom 10-20% of the plates.

As an alternative, the dividing wall 18 can also extend down to the floor of the bottom; cf. example in FIG. 4.

In the example of FIG. 5, the distillation column 12 is additionally provided with a barrier wall 21 which closes off the part of the distillation column 12 located on the side of the side offtake 13 from the dividing wall-free top region 19.

In all embodiments of the dividing wall columns (FIGS. 3 to 5), the dividing wall 18 runs essentially vertically through the distillation column 12 and not centrally so that the ratio of the area on the side of the side offtake to the area on the side of the feed point for the bottom product is 0.5. However, other area ratios can also be set via the position of the dividing wall, for instance in the range from 0.1 to 0.9, preferably from 0.25 to 0.75 and very particularly preferably from 0.4 to 0.6.

In the dividing wall-free top region 19, the liquid is divided in a ratio of from 0.5 to 1, preferably from 0.5 to 0.8, between the side of the side offtake 13 and the side of the inflowing bottom product 9.

LIST OF REFERENCE NUMERALS

1 Composition
2 Quenching column
3 Aqueous liquid stream
4 Liquid solution
5 Gas stream
6 Dewatering column
7 Entrainer
8 Water/entrainer azeotrope
9 Bottom product
10 Decanter
11 Wastewater
12 Distillation column
13 Side offtake
14 Acrylic acid
15 Low boilers (acetic acid)
16 High boilers (aldehyde)
17 Inhibitor
18 Dividing wall
19 Dividing wall-free top region
20 Dividing wall-free bottom region
21 Barrier wall

The invention claimed is:

1. A process for separating acrylic acid from a composition that comprises acrylic acid and an accompanying product, the process comprising:
   first, contacting the composition with an aqueous liquid stream, thereby obtaining a liquid solution comprising acrylic acid, accompanying product, and water,
   adding an entrainer to the liquid solution, thereby obtaining a heterogeneous minimum azeotrope with the water of the liquid solution,
   separating the liquid solution by distillation into an overhead product comprising the minimum azeotrope and a bottom product comprising acrylic acid and the accompanying product,
   separating the overhead product into water and a recirculatable entrainer, and
   separating the bottom product by distillation into acrylic acid and the accompanying product,
   wherein separating the bottom product comprises:
   introducing and separating the bottom product in a distillation column that comprises a side offtake,
   taking off high-boiling constituents of the accompanying product from a bottom of the distillation column,
   taking off low-boiling constituents of the accompanying product from a top of the distillation column, and
   taking off the acrylic acid from the side offtake,
   wherein taking off the acrylic acid from the side offtake comprises taking off the acrylic acid from the side offtake in a liquid form,
   wherein the distillation column is a dividing wall column comprising a dividing wall extending essentially vertically through the column,
   wherein the dividing wall extends from a dividing wall-free top region to a dividing wall-free bottom region or to a floor of a bottom, and
   wherein the distillation column further comprises a barrier wall that is constructed to close off a part of the distillation column located on a side of the side offtake from the dividing wall-free top region.

2. The process according to claim 1, wherein the dividing wall extends from a height level above a level of the side offtake, and
   wherein the dividing wall is configured to extend to a height level below a level of the bottom product introduced into the distillation column.

3. The process according to claim 1, wherein the accompanying product comprises at least one component selected from the group consisting of acetic acid, water, and an aldehyde.

4. The process according to claim 1, wherein the entrainer is an organic solvent having a boiling point of from 80 to 130° C.

5. The process of claim 4, wherein the entrainer comprises at least one component selected from the group consisting of toluene, heptane, cyclohexane, and methylcyclohexane.

6. The process according to claim 1,
   wherein the separating the overhead product into water and a recirculatable entrainer comprises distilling in a dewatering column such that a concentration of water in the bottom product is less than 0.5% by weight and a concentration of the entrainer in the bottom product is from 1 to 15% by weight.

7. The process of claim 6, wherein the concentration of the entrainer in the bottom product after the separating the liquid solution is from 8 to 12% by weight.

8. The process of claim 6, wherein the concentration of water in the bottom product after the separating the liquid solution is from 0.05% to 0.3% by weight.

\* \* \* \* \*